United States Patent [19]

Reinicke

[11] Patent Number: 4,834,704
[45] Date of Patent: May 30, 1989

[54] INJECTABLE INFUSION PUMP APPARATUS FOR IMPLANTING LONG-TERM DISPENSING MODULE AND MEDICATION IN AN ANIMAL AND METHOD THEREFOR

[75] Inventor: Robert H. Reinicke, Mission Viego, Calif.

[73] Assignee: Eaton Corporation, Cleveland, Ohio

[21] Appl. No.: 181,134

[22] Filed: Apr. 13, 1988

[51] Int. Cl.$^4$ .............................................. A61M 5/00
[52] U.S. Cl. ...................................... 604/51; 604/57; 604/132; 604/891.1
[58] Field of Search ....................... 604/57, 59, 60, 93, 604/96, 103, 132, 891.1, 51; 128/DIG. 2

[56] References Cited

U.S. PATENT DOCUMENTS

| | | | |
|---|---|---|---|
| Re. 32,348 | 2/1987 | Pevsner | 604/103 X |
| 3,469,578 | 9/1969 | Bierman | |
| 3,817,248 | 6/1974 | Buckles et al. | |
| 3,846,539 | 12/1969 | Jacuzzi | 141/329 |
| 3,993,069 | 11/1976 | Buckles et al. | |
| 4,318,400 | 3/1982 | Peery et al. | |
| 4,386,929 | 6/1983 | Peery et al. | 604/132 |
| 4,419,096 | 12/1983 | Leeper et al. | 604/132 |
| 4,425,117 | 1/1984 | Hugemann et al. | 604/132 X |

Primary Examiner—Stephen C. Pellegrino
Attorney, Agent, or Firm—L. G. Vande Zande

[57] ABSTRACT

A two-stage injection device has a resiliently expandable medication reservoir stored in collapsed state within the cannula. After inserting the cannula through the skin into an animal cavity, depression of a first stage element injects the reservoir out the cannula into the cavity. Depression of a second stage element fills the reservoir with fluid medication, elastically expanding the reservoir. The injection apparatus is withdrawn, leaving the reservoir implanted in the cavity, continuously infusing medication for a period up to hundreds of days through a restrictor orifice under the pressure of the elastically stretched walls of the reservoir.

13 Claims, 3 Drawing Sheets

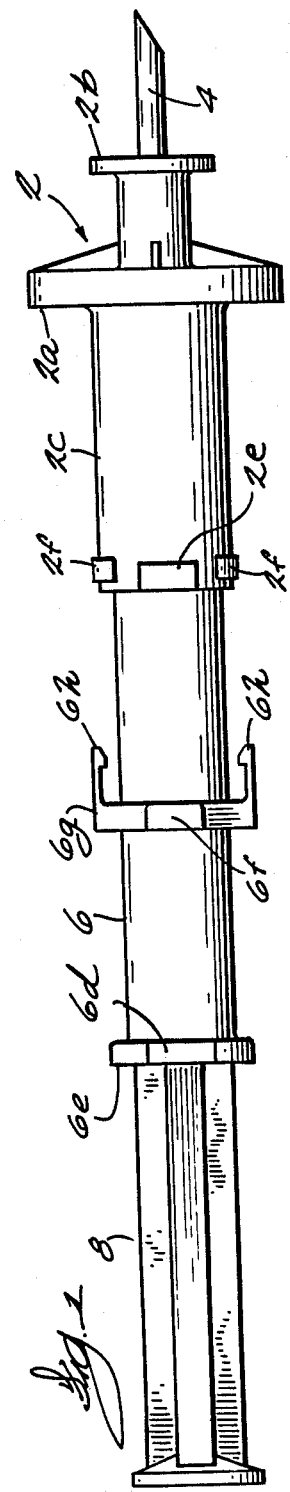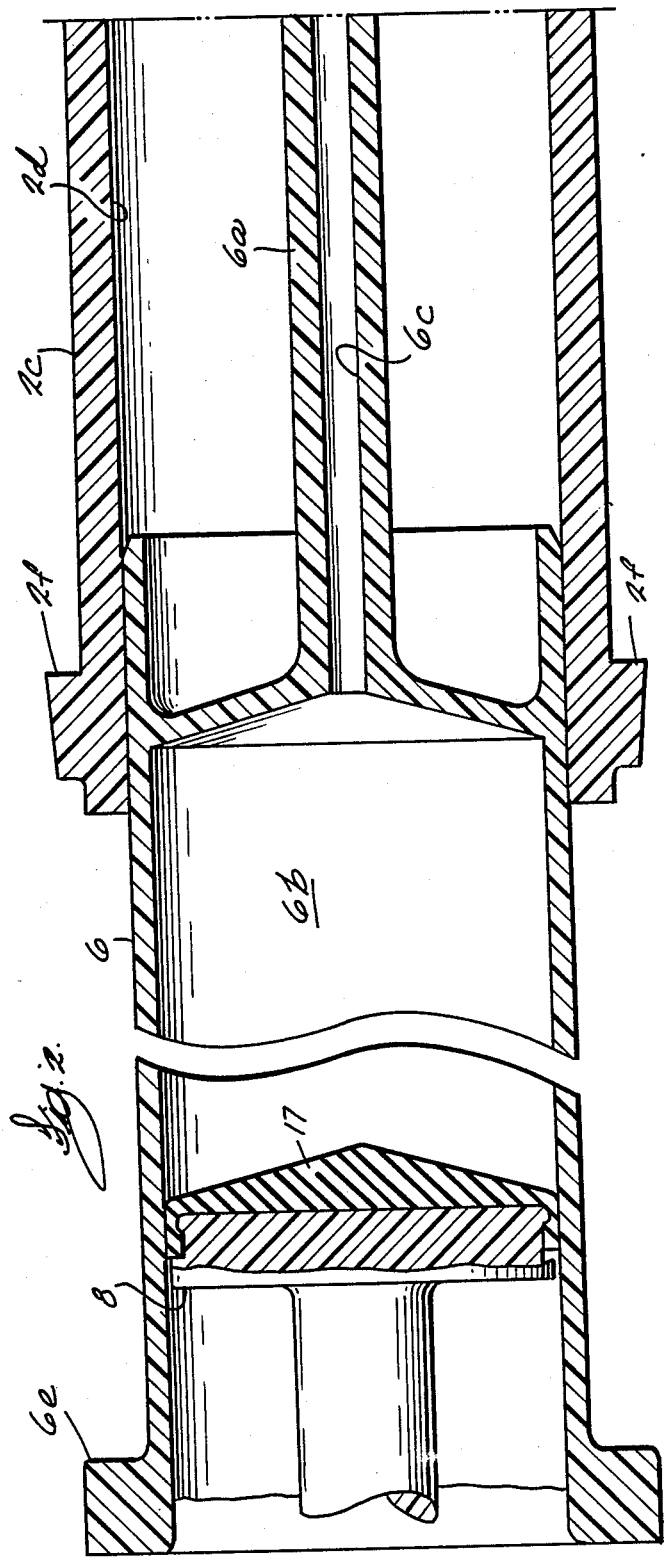

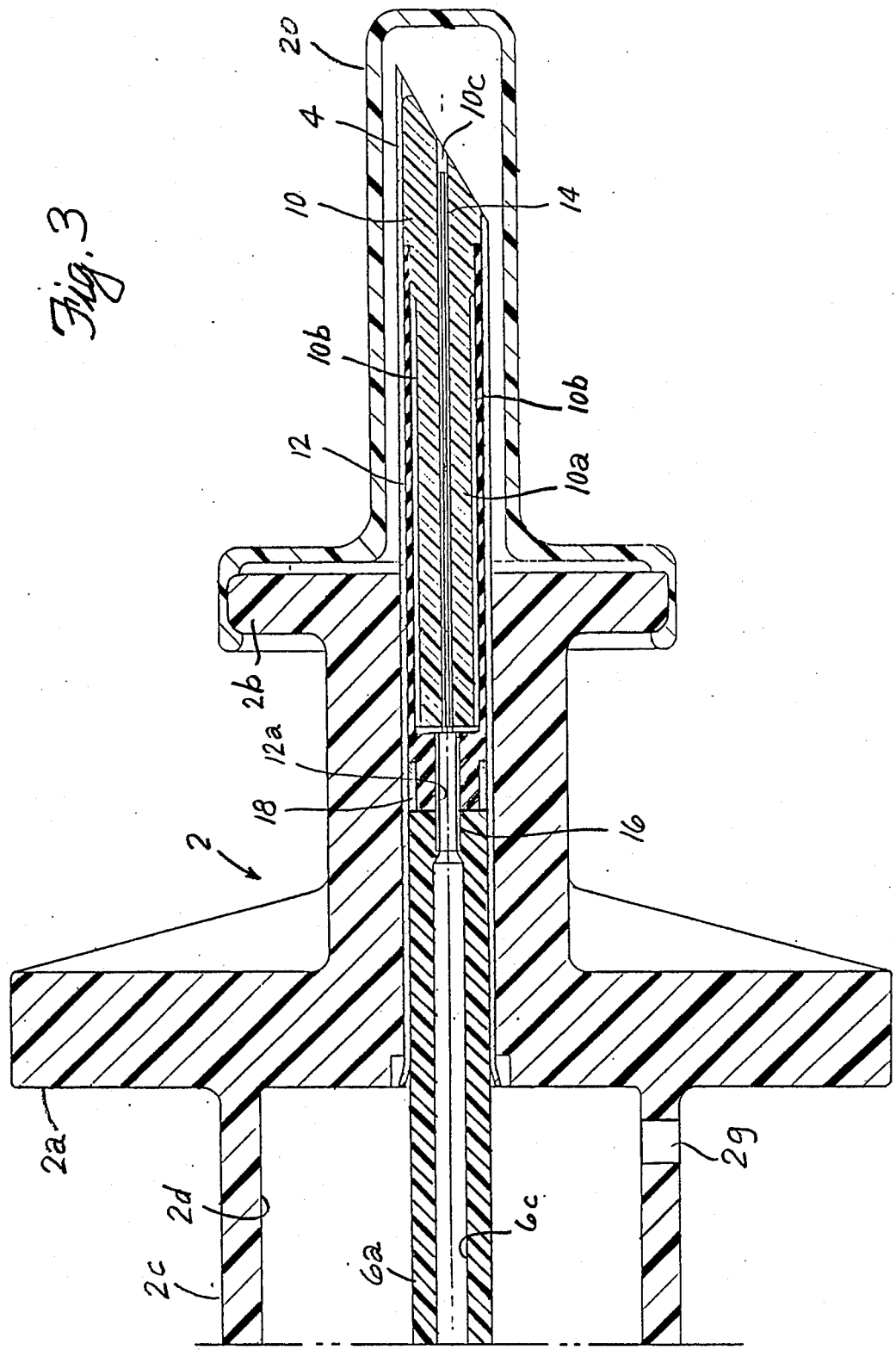

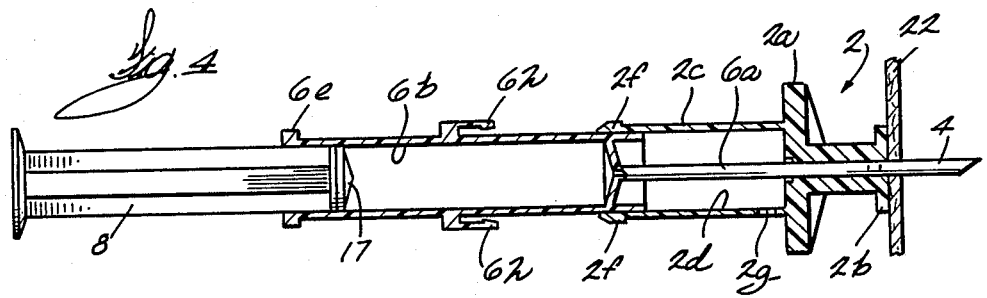
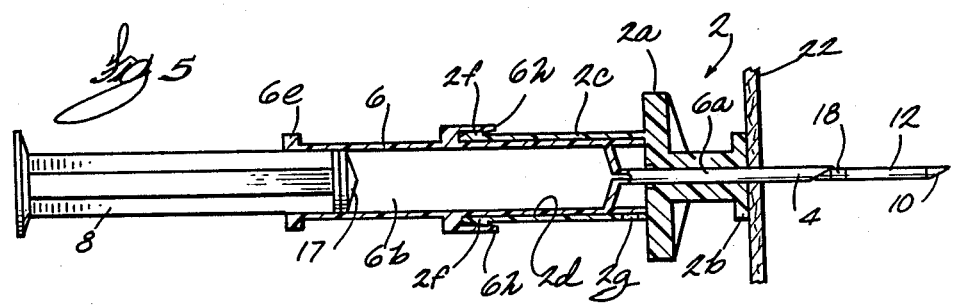
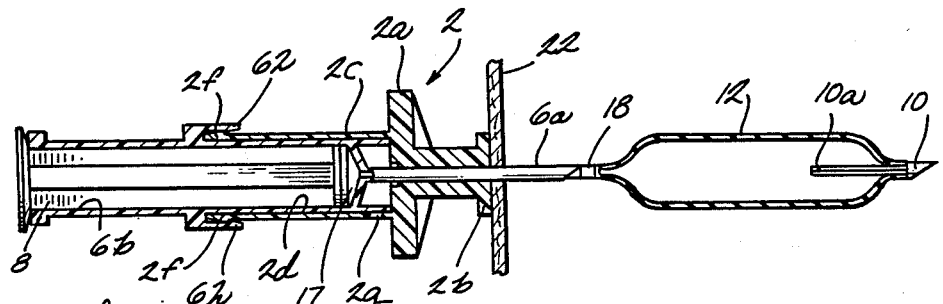
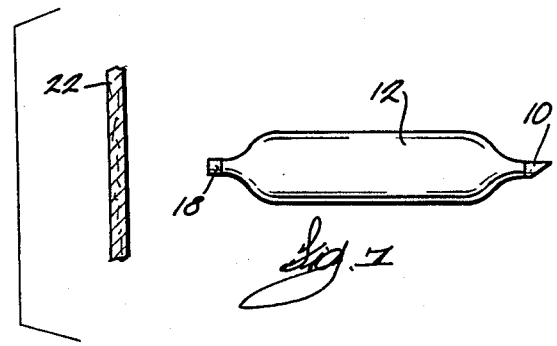

INJECTABLE INFUSION PUMP APPARATUS FOR IMPLANTING LONG-TERM DISPENSING MODULE AND MEDICATION IN AN ANIMAL AND METHOD THEREFOR

BACKGROUND OF THE INVENTION

The present invention relates to implantable medication infusion pump devices and, more particularly, to a device of this type which may be injected into the body of an animal. The invention also relates to apparatus for injecting the infusion pump device and to a method therefor.

It is known that infusion of growth hormones produced by recombinant DNA and possibly other drugs provide benefit in animals such as increased quantity of milk production in cows, larger growth of the animals to increase weight and edible meat, a reduced fat content of meat and an improved feed efficiency for the animals, among other things. Presently, such drugs are injected into the animals as often as once a day by syringe/needle bolus injections. Such procedures are time consuming and costly.

In my copending United States patent application entitled "Implantable Medication Infusion Device and Bolus Generator Therefor", Ser. No. 162,766 filed Mar. 1, 1988, I describe an implantable medication infusion pump device of the continuous flow type which is surgically implanted into the body cavity of an animal such as a cow or a hog. The device described therein is an inexpensive drug infusion device made of non-metallic parts, primarily of molded plastic and rubber parts. The device is implanted next to the skin of the animal such that it may be refilled by percutaneous syringe/needle injection. It has a drug capacity which lasts several months and therefore requires refilling only once ever several months. Pressurized air or inert gas is used as a propellant acting upon a medication reservoir for forcing the drug out of the device to the infusion site. The reservoir comprises a flexible bladder restrained from elastically expanding by the pump structure so as not to add contraction forces of a stretched bladder wall to the pressure generated by the compressed air or inert gas, thereby rendering the force on the medication essentially constant. A flow restrictor is incorporated in an outlet of the device to regulate the drug dosage which is delivered to the infusion site by a catheter connected to the outlet.

The aforedescribed invention of my copending application avoids the nuisance, expense and high possibility of infection attendant with daily injections of growth hormones for hundreds of days. However, that device does require a trained surgeon for implanting the device. The costs of such surgical implantation may significantly reduce the cost benefit derived from the medication dosages.

SUMMARY OF THE INVENTION

This invention realized the benefits of an implantable long-term medication dispensing infusion pump device without requiring surgical techniques. It provides a drug infusion pump module that is implantable by injection, filled with a medication as an integral step in the injection process, and automatically provides continuous infusion of the medication for a period of several months. The invention comprises a two-stage syringe/needle injection device having a resilient expandable medication reservoir stored within the cannula. The cannula is inserted through the skin of the animal into a body cavity. A syringe barrel 6 is depressed into a main body of the device as a first stage to eject the resilient reservoir into the animal's body cavity. A plunger of the syringe is subsequently depressed as a second stage to injection medication into the resilient reservoir, thereby expanding the reservoir by elastically stretching the walls thereof. The cannula is then withdrawn from the animal, separating it from the expanded reservoir which remains in the animal as an infusion pump module dispensing medication into the animal at a predetermined rate through a flow restrictor in the medication reservoir.

The invention and its advantages will become more readily apparent when reading the following description and claims in conjunction with the accompanying drawings.

BRIEF DESCRIPTION OF THE DRAWINGS

FIG. 1 is a side elevation view of the injectable infusion pump apparatus of this invention shown in a fully extended, prefilled condition ready for application to an animal;

FIGS. 2 and 3, when taken together with the left-hand end of FIG. 3 placed adjacent the right-hand end of FIG. 2, is a cross sectional view of the apparatus of FIG. 1 with certain sections removed to reduce the overall length of the figures;

FIG. 4 is a schematic illustration of the apparatus of FIGS. 1-3 injected through the hide of an animal;

FIG. 5 is a schematic illustration similar to FIG. 4, showing the apparatus depressed in its first stage to inject a resilient expandable reservoir pump module into a body cavity of the animal;

FIG. 6 is a schematic illustration similar to FIG. 5 showing the apparatus fully depressed in its second stage to fill and expand the medication reservoir within the body cavity of the animal; and FIG. 7 is a schematic illustration similar to FIG. 6 showing the apparatus withdrawn from the animal and the filled reservoir remaining in place within the body cavity of the animal.

DESCRIPTION OF THE PREFERRED EMBODIMENTS

As seen in FIG. 1, the injectable infusion pump apparatus of this invention comprises a main body portion 2 which is an elongated, generally cylindrical structure of molded plastic or the like. Main body 2 has a disc-shaped flange 2a ntermediate its ends and a smaller disc flange 2b at its right end. A stainless steel cannula 4 is molded into main body 2 to extend from the right-hand end thereof adjacent flange 2b. The distal end of cannula 4 is cut at an acute angle and sharpened to a beveled point typical of syringe needles to facilitate puncture and penetration of the hide, or skin, of the animal. The left-hand end of main body 2 comprises a hollow generally cylindrical guide 2c for receiving a syringe barrel 6 therein. A plunger 8 is telescopically received within an internal bore of syringe barrel 6 in a well known manner.

Referring also to FIGS. 2 and 3, the injectable infusion pump apparatus will be described in more particular detail. With reference to FIG. 3, an elongated, generally cylindrical plastic plug 10 is inserted into an open right-hand end of a resilient sleeve 12 formed of Latex elastomer or the like. Sleeve 12 is bonded to plug 10 to seal off the right-hand end of sleeve 12. A stem 10a of plug 10 projects leftwardly within the sleeve 12 to a point near the left-hand end of the sleeve which is formed in a thick cylindrical mass to provide a self-sealable septum which may preferably have a slit 12a therein. The surface of stem 10a is provided with a plurality of elongated grooves 10b therein which form fluid flow passages between the elastomer sleeve 12 and the stem 10a. An axial opening 10c is provided within plug 10 to extend from end to end thereof. Opening 10c preferably has a thin metal capillary tube 14 insert molded therein to provide a flow restriction orifice in plug 10. The right-hand end of plug 10 is formed at an acute angle to be flush with the distal end of cannula 4.

Syringe barrel 6 is inserted within the open left-hand end of a chamber 2d of hollow cylindrical guide 2c. Syringe barrel 6 has a tubular extension 6a projecting from its right-hand end which in turn has a small diameter stainless steel tube 16 molded integrally therewith to project beyond the distal end of extension 6a. Tube 16 is inserted into slit 12a of the elastomer sleeve 12. A spring clamp 18 is provided around the elastomer sleeve 12 at the septum end to affix elastomer sleeve 12 to stainless steel tube 16. This assembly is inserted within main body 2 and cannula 4 such that plug 10, elastomer sleeve 12 and the right-hand end of projection 6a are disposed within the cannula 4.

Syringe barrel 6 is a hollow member having a generally cylindrical chamber 6b at its left-hand end. An axial passageway 6c is provided in extension 6a to communicate with an axial opening through tube 16. Plunger 8 is disposed within the chamber 6b of syringe barrel 6 and has a rubber seal 17 affixed over its internal end to provide a sliding, fluid tight seal between the plunger 8 and syringe barrel 6.

Referring again to FIG. 1, syringe barrel 6 has a pair of laterally extending wings 6d (only one of which is visible) formed on a flange 6e at the left-hand end of barrel 6. A second pair of laterally extending wings 6f (only one of which is visible) is provided on a flange 6g formed on an intermediate portion of syringe barrel 6. Flange 6g also has a pair of diametrically spaced resilient hooks 6h extending toward main body 2. The left-hand end of cylindrical guide 2c of main body 2 is provided with a pair of laterally projecting wings 2e (only one of which is visible) and a pair of radially projecting catch members 2f formed at diametrically spaced intervals on the body. The catch members 2f are beveled leftwardly to cooperate with hooks 6h in a manner to be described hereinafter.

The apparatus assembled as hereinbefore described in then filled with a drug using a vacuum filling procedure to first evacuate air inside the syringe barrel 6b, the passageway 6c within extension 6a and tube 16, and the interior of elastomer sleeve 12. By this procedure, the entire device is filled with a fluid drug that is void of any air or vapor bubbles that will disrupt the accuracy of flow thereof through the restrictor passage orifice in capillary tube 14. When thus filled, a protective plastic cap 20 is positioned over cannula 4 and snap-fit attached to flange 2a of main body 2. In a preferred embodiment, the entire apparatus is subsequently packaged in a sterile plastic bag for shipping, storing and handling prior to its use.

When it is desired to inject an animal, the bag and plastic cap 20 are removed and discarded. The user, by grasping the main body 2 near flange 2a, injects cannula 4 through the hide or skin 22 of the animal (FIG. 4) at a site where the cannular can enter the peritoneal or other like cavity without striking an animal organ. The depth of cannula penetration is limited to about one inch or less when the flange 2b of body 2 stops against the animal hide. The beveled end of plug 10, being flush with the beveled end of cannula 4, prevents coring of the hide or flesh inside of the cannula. Although the cannula can be as large as approximately 0.300 inch in diameter for injection into a large animal such as a cow, it is small enough to easily penetrate the anmial hide covering the peritoneal cavity.

Following cannula insertion, the user grasps wings 6f and 2e (FIG. 1) and depresses the syringe barrel 6 within chamber 2d of main body 2 as shown in FIG. 5. One or more openings 2g may be provided in guide 2c to exhaust air from chamber 2d if sufficient clearance is not provided between barrel 6 and chamber 2d. When barrel 6 is fully depressed, hooks 6h engage and snap over catches 2f on main body 2 to secure the syringe barrel 6 in its depressed condition with respect to main body 2. This action also causes extension 6a to force elastomer sleeve 12 and plug 10 out the distal end of cannula 4 as a module to enter the cavity of the animal. Next, the user grasps wings 6d of syringe barrel 6 with his fingers and depresses plunger 8 within chamber 6b with his thumbs acting on the left-hand end of plunger 8. This movement forces the fluid medication through the passageway 6c and passage in tube 16 into the elastomer sleeve 12 and grooves 10b f stem 10a to cause the elastomer sleeve 12 to elastically expand as a medication reservoir as shown in FIG. 6. The Latex elastomer expands due to the pressurization formed by the depression of plunger 8 within syringe barrel 6 to form a generally cylindrical balloon reservoir which contains the drug. By way of example, using an initial unpressurized Latex elastomer wall thickness of approximately 0.040 inch, a 0.25 inch outside diameter, sleeve 12 starts to expand at about 10 psig and then quickly drops to about 8 psig and continues to form a balloon reservoir at about 8 psig pressure throughout virtually all of the filling cycle. The user exerts a force of about 17 pounds to introduce drug into the elastomer sleeve. This force is sufficient to both overcome the 8 psig back pressure required to continuously expand the sleeve of this particular example and to overcome the pressure drop in the drug flow passage from the syringe barrel into the sleeve needed to fill the balloon reservoir with 50 ml of drug in one minute. Virtually all of this pressure drop occurs in the flow restriction of the tube 16 that penetrates the septum end of the sleeve 12. In this example, tube 16 has a 0.055 inch interal diameter by 0.25 inch long. A drug with a viscosity of 2000 centipoise and 62.4 pounds per cubic foot density is used. The pressure drop in tube 16 is 12 psi to transfer 50 ml of the drug in one minute. Thus, the pressure generated by pushing the syringe plunger 8 is the pressure needed to expand the Latex elastomer sleeve 12 (8 psig) plus the pressure drop, (12 psi) for a total of 20 psig. This pressure, acting on the one inch diameter plunger piston area of 0.785 square inches plus one pound for plunger seal 17 friction equals the 17 pound plunger force level for this particular design example. The 17 pound syringe plunger force is reasonable since it is needed for only one minute and can be manually applied with both hands. A motor or pneumatic actuator could be used to apply the piston force especially if a large number of animals are to be implanted.

When the entire quantity of medication is injected into the reservoir formed by plug 10, elastomer sleeve 12 and clamp 18 as seen in FIG. 6, the main body 2, syringe barrel 6 and plunger 8 may be withdrawn from the animal, removing therewith tube 16 from the septum 12a of elastomer sleeve 12. The septum re-seals either under its own characteristics or with the assistance of clamp 18 to seal off the septum end of sleeve 12. The 8 psig pressure exerted on the drug by the elastic stretch of the balloon forces drug to flow out the stainless steel flow restrictor tube 14 and into the peritoneal cavity. By example, a 0.011 inch inside diameter by 2 inch long restrictor tube controls the infusion rate of the aforedescribed drug to 0.38 ml/day. This infuses the 50 ml drug volume in the reservoir continuously over a 133 day period. The inside diameter of the flow restrictor tube 14 is sufficiently large so that it will not clog, even without using a filter. When all of the drug is expelled and the expandable elastomer sleeve returns to its original unpressurized state, the plug and tube module is approximately 0.25 inch diameter by 2.25 inches long. This is a relatively small object compared to the size of the peritoneal cavity of the average dairy cow. It is anticipated that smaller devices would be utilized for smaller animals such as hogs. The spent implanted module is made entirely of biocompatable materials such as medical grade polysulfone or the like, medical grade Latex or silicon elastomer or the like and medical grade stainless steel. As such it need not be removed from the animal, thus avoiding the nuisance and expense of locating and surgically explanting the spent module. Additional new pump modules would simply be implanted if and as needed and spent modules would remain in the peritoneal cavity. If the animal is to be slaughtered for its edible meat, residual spent modules would not be of concern since they are not within the animal meat.

While the foregoing has described a preferred embodiment of the injectable infusion pump apparatus, dispensing module and method of using, it is to be understood that the invention is susceptible of various modifications without departing from the scope of the appended claims.

I claim:

1. Injectable infusion pump apparatus for implanting a long-term dispensing module and medication into a body cavity of an animal comprising:
    an elongate body having a cannula extending from one end and a chamber communicating with said cannula open to an opposite end, the distal end of said cannula being cut at an acute angle;
    a plug slidably retained within said cannula, said plug having a fluid flow restrictor orifice therethrough;
    a hollow elastic reservoir having said plug affixed in one end to seal off said one end and having a self-sealing septum at an opposite end, said reservoir being disposed within said cannula;
    a syringe barrel slidably disposed in said chamber having a tubular extension projecting into said cannula abutting said opposite end of said reservoir, the distal end of said extension having a reduced-size projection penetrating said septum, said syringe barrel having a fluid receiving cavity and a fluid flow passage leading therefrom through said tubular extension and said reduced-size projection into said reservoir;
    a quantity of fluid medication in said syringe barrel cavity; and
    a plunger slidably disposed in said syringe barrel cavity;
    depression of said syringe barrel into said body chamber causing said extension to eject said reservoir and said plug out the distal end of said cannula; and
    depression of said plunger into said syringe barrel cavity injecting said medication into said reservoir through said fluid flow passage to elastically expand said reservoir, elasticity of said expanded reservoir providing a pressure on medication therein to force said medication through said flow restrictor orifice at a predetermined rate.

2. The injectable infusion pump apparatus as defined in claim 1 wherein said plug has an elongated stem portion extending within said reservoir toward said opposite end of said reservoir, said stem terminating in spaced relation to an internal end of said reduced-size projection.

3. The injectable infusion pump apparatus as defined in claim 2 wherein said flow restrictor orifice comprises an elongated capillary passageway extending through said plug.

4. The injectable infusion pump apparatus as defined in claim 2 wherein said stem has a plurality of grooves in an external surface of said stem.

5. The injectable infusion pump apparatus as defined in claim 4 wherein said reservoir is in intimate contact with said stem along its length and said grooves form fluid flow passageways toward said one end of said reservoir.

6. The injectable influsion pump apparatus as defined in claim 1 wherein an external end of said plug is formed at an acute angle to be substantially flush with said distal end of said cannula.

7. The injectable infusion pump apparatus as defined in claim 1 further comprising clamping means disposed around said opposite end of said reservoir exerting a closing force on said septum.

8. The injectable infusion pump apparatus as defined in claim 1 wherein said reduced-size projection comprises a tube affixed in the distal end of said extension.

9. The injectable infusion pump apparatus as defined in claim 1 further comprising locking means on said body and said syringe barrel cooperably engagable when said syringe barrel is depressed a predetermined amount to lock said syringe barrel depressed.

10. The injectable infusion pump apparatus as defined in claim 9 wherein said locking means automatically engages by depressing said syringe barrel said predetermined amount.

11. The injectable infusion pump apparatus as defined in claim 10 wherein said locking means comprises resilient hooks on said syringe barrel deflected into locking engagement with catch means on said body upon depression of said syringe barrel said predetermined amount.

12. The injectable infusion pump apparatus as defined in claim 1 wherein said body and said syringe barrel are provided with finger grip means to faciliate depression of said syringe barrel into said body.

13. A method of injecting a long-term dispensing module and medication into an animal comprising:
    providing injectable infusion pump apparatus as defined in claim 1;
    inserting said cannula into a body cavity of an animal by penetrating body tissue covering said body cavity;

depressing said syringe barrel into said chamber to eject said reservoir and said plug from said cannula through said distal end of said cannula;

depressing said plunger into said syringe barrel cavity to inject medication from said cavity through said fluid flow passageway into said reservoir, thereby elastically expanding said reservoir; and withdrawing said cannula from said animal body cavity, thereby separating said tubular extension and said reservoir and removing said reduced-size projection from said septum;

said reservoir elastically contracting to force said medication through said flow restrictor orifice at a predetermined rate.

* * * * *